United States Patent [19]

Tsuchino

[11] Patent Number: 5,307,396
[45] Date of Patent: Apr. 26, 1994

[54] RADIATION IMAGE PICKUP METHOD AND APPARATUS

[75] Inventor: Hisanori Tsuchino, Hino, Japan

[73] Assignee: Konica Corporation, Tokyo, Japan

[21] Appl. No.: 982,781

[22] Filed: Nov. 30, 1992

Related U.S. Application Data

[63] Continuation-in-part of Ser. No. 727,570, Jul. 9, 1991, abandoned.

[51] Int. Cl.$^5$ .............................................. G21K 5/10
[52] U.S. Cl. ...................................... 378/146; 348/77
[58] Field of Search ................................... 378/146, 99

[56] References Cited

U.S. PATENT DOCUMENTS 4,868,857 9/1989 Dobbins ................................. 378/99

FOREIGN PATENT DOCUMENTS 62-129034 6/1987 Japan ..................................... 378/146

*Primary Examiner*—Craig E. Church
*Attorney, Agent, or Firm*—Jordan B. Bierman

[57] ABSTRACT

In picking up a radiation image, and image is first picked up without adjusting the radiation dose of a radiation beam that scans an irradiation target to thereby acquire information of the dose of radiation transmitted through the irradiation target at the same time the image is picked up. Based on the information of the transmitted dose of radiation, the radiation dose to be controlled is determined, and image pickup is executed again to be superimposed on the initial pickup while controlling the radiation dose according to the determined control dose, whereby the radiation image data is obtained. Further, the image of the case where the radiation dose is not controlled is restored in signal processing of the obtained radiation image data and the data of the radiation control quantity.

20 Claims, 8 Drawing Sheets

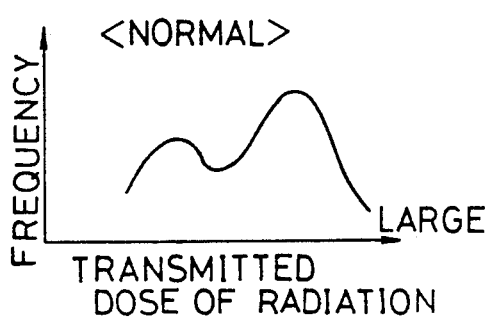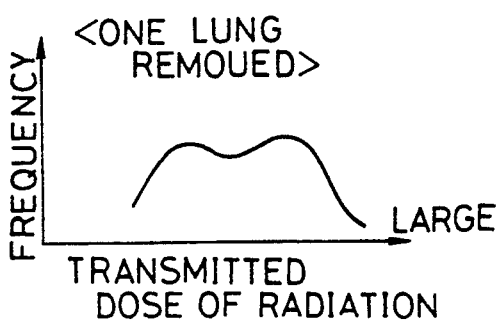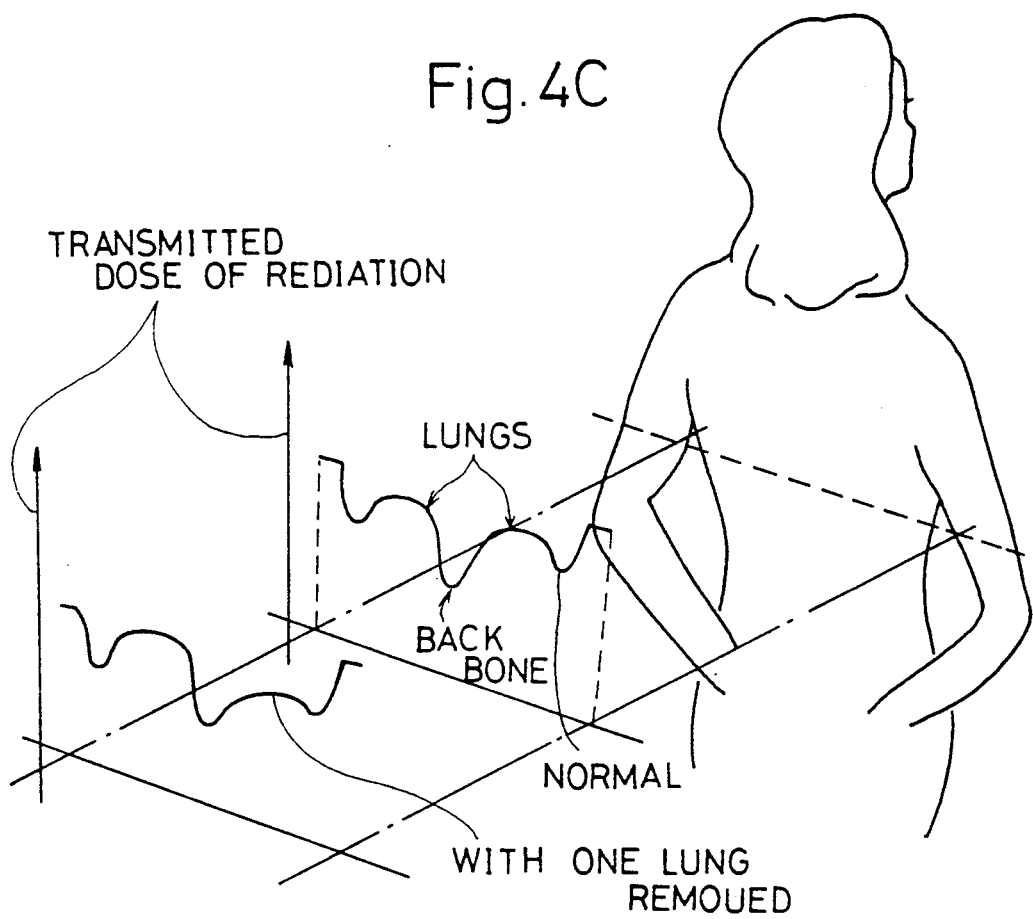

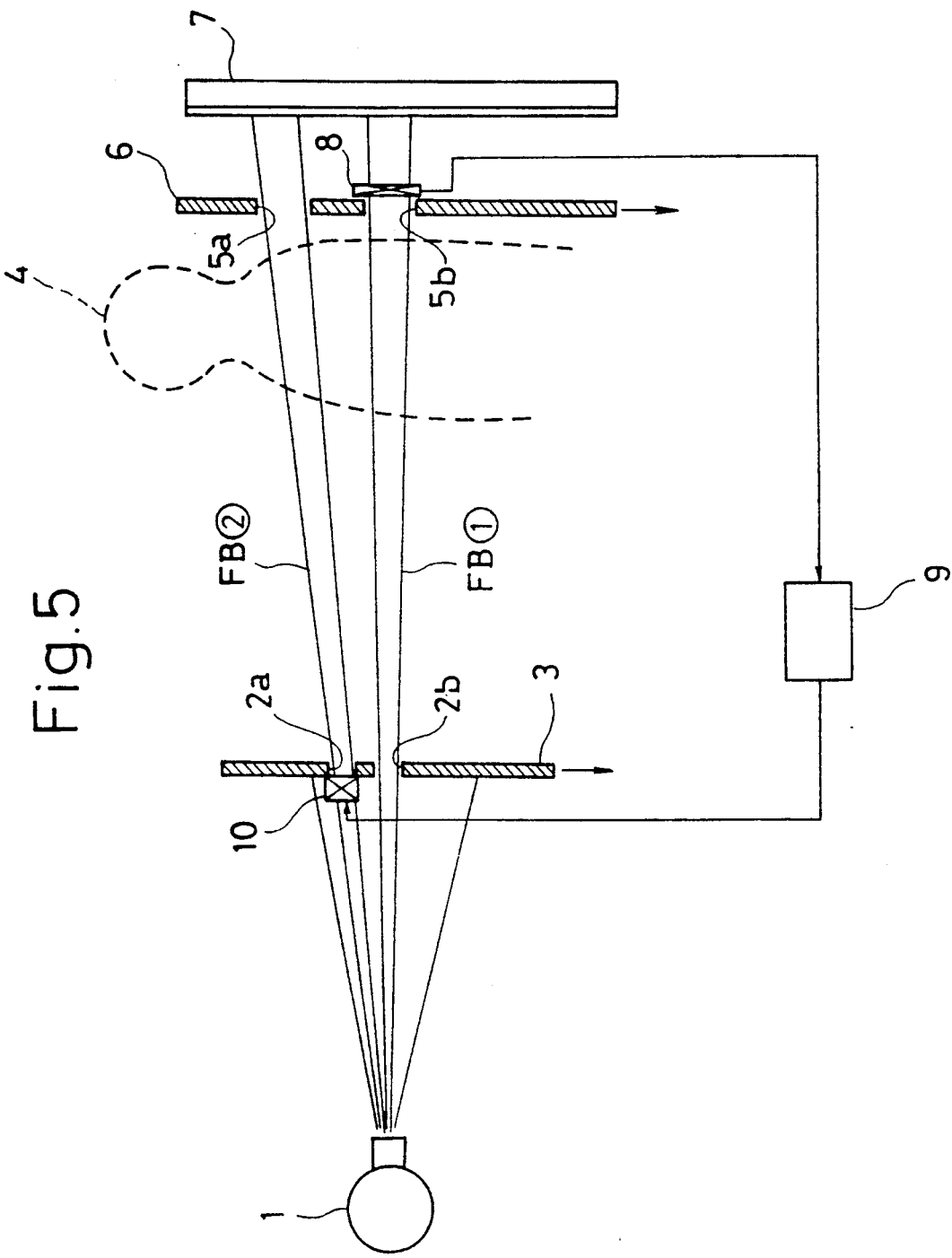

RADIATION IMAGE PICKUP METHOD AND APPARATUS

This application is a continuation-in-part application of Ser. No. 07/727,570, filed on Jul. 9, 1991 now abandoned.

BACKGROUND OF THE INVENTION

(1) Field of the Invention

The present invention relates to a radiation image pickup method and apparatus f o r acquiring a radiation image corresponding to the dose of radiation transmitted through an individual portion of an irradiation target. More particularly, this invention pertains to an arrangement which ensures control of the exposure for compensation for exposure.

(2) Description of the Related Art

A radiation image pickup apparatus comprises a radiation source, which is typically an X-ray tube, and an image pickup/recording device for detecting the radiation amount from the radiation source, which has been passed through an irradiation target, to pick up and record its corresponding radiation image. As the image pickup/recording device, a radiation sensitive film, a fluorescent display screen, and electronic image amplifying tube or the like may be used.

According to such a radiation image pickup apparatus, when a given dose of radiation is irradiated on individual portions of the irradiation target, proper exposure will result for some portions while underexposure will be caused for others due to the difference in the radiation absorbency of the individual portions. This phenomenon lowers the signal level corresponding to the underexposed portions in a device for photoelectrically reading a radiation projected image, or drops the density of the underexposed portion on an X-ray photograph. In either case, it is not possible to acquire sufficiently a desired amount of information for the under-exposed portion.

In photographing the chest portion of a human body with, for example, and X-ray examination apparatus used for medical purposes, therefore, it is not easy to reproduce both the image of such a portion as a lung, which easily passes radiation therethrough, and the image of such a portion as a backbone or abdomen, which does not allow easy transmission of the radiation, in a manner that permits easy simultaneous observation of these portions.

There is a conventional system which controls the exposure for each portion of the irradiation target in the following manner to acquire a proper exposure for that portion (see Japanese Unexamined Patent Publication No. Sho 62-129034).

The mechanism of controlling the exposure may be designed so that a fan-beam forming slit formed in a collimator provided between a radiation source and the irradiation target is provided with multiple shutter members arranged lengthwise of the slit and supported in such a manner as to be movable across the slit.

This mechanism scans a fan beam in a direction perpendicular to the lengthwise of the slit to irradiate radiation on the irradiation target, and detects the dose of radiation transmitted through the individual portions of the target. The mechanism then controls the amount of the diaphragm of the radiation by the shutter members (or the amount of the diaphragm of the slit area) based on the results of the detection to thereby permit image pickup while controlling the exposure to each portion of the target.

According to the above-described system which properly controls the exposure (the exposure to the irradiation target) by adjusting the opening area of the fan-beam forming slit, while a film or the like is exposed, the slit's opening area is immediately controlled on the basis of the dose of the exposure radiation, or the adjusting dose of radiation at the actual image-pickup is acquired from preacquired information of the dose of radiation transmitted through the irradiation target, so that the image pickup is carried out separately by controlling the radiation dose based on the control dose.

In either case, according to the prior art, an image is picked up by a single irradiation executed while controlling the exposure to the irradiation target. To secure the maximum value of radiation dose necessary for the irradiation target (the radiation dose necessary for the proper exposure at a portion which least passes radiation through), therefore, the output of the radiation source is kept large for the image pickup. For an irradiation target whose average level of the necessary dose of radiation is small, image pickup is executed with a large dose of radiation cut down. This method is likely to waste much portion of the radiation dose from the radiation source and naturally puts a large burden on radiation generated from the radiation source.

When there is some portion for which compensation for exposure variation, if any is not desirable, or when there is an image for which no compensation for exposure should be made at all, the prior art cannot automatically cope with either case, and requires that, for example, an operator (photographer) determine in advance a region for the compensation for exposure, or operate a switch to cancel the compensation. The required operation is troublesome and increases a burden on the operator to determine such a region.

Particularly, in an X-ray examination apparatus available for medical purposes, if the difference in exposure caused by some disease is compensated for, medical diagnoses of the disease may be adversely affected. In this respect, there is a demand for a system that can control the radiation dose in different ways, but the conventional apparatus has had difficulty in fulfilling such demand.

SUMMARY OF THE INVENTION

The present invention has been made with a view to solving the above problems and it is an object of the invention to provide suppression over the dose of radiation generated from a radiation source in pickup of a radiation projected image wherein the proper exposure is acquired by controlling the exposure to an irradiation target based on information of the exposure transmitted through the target.

It is another object of the present invention to provide a control capable of discriminating for each irradiation target whether to control the exposure to the irradiation target only at necessary portions thereof or to perform no control of the exposure at all in picking up an image, thereby ensuring automatic radiation control.

It is a further object of the present invention to ensure a quick pickup of a radiation projection image, which can achieve the above objects.

To achieve these objects, according to a radiation image pickup method and apparatus of the present invention, an image is first picked up without adjusting the dose of a radiation beam that scans an irradiation target to thereby acquire information of the transmitted dose of radiation according to the image pickup.

Based on the information of the transmitted dose of radiation, the radiation dose to be controlled is then determined, and image pickup is executed again to be superimposed on the initial pickup while controlling the radiation dose according to the determined control dose, so that a final radiation projected image is obtained from the multiple-image pickup (multi-exposure) which consists of the first image picked up without the radiation adjustment and the second image picked up with the radiation adjustment.

With the above arrangement that provides a radiation projected image from the multiple image pickup, image pickup is executed while controlling the exposure based on the information of the transmitted dose of radiation to thereby acquire the proper exposure for an individual portion of the irradiation target, and irradiation is divided into several runs. It is therefore possible to secure the necessary radiation dose even if the radiation dose from the radiation source for each image pickup is reduced.

The arrangement may be modified such that while the dose of radiation to be controlled is determined on the basis of the information of the transmitted dose of radiation acquired in the first image pickup conducted with a radiation beam having a given radiation dose, and image-pickup portion which requires no adjustment of the radiation dose is determined so that no radiation adjustment is performed on this portion even the dose of radiation adjustment for the portion has been determined.

This arrangement can prevent adjustment of the radiation dose for a portion requiring no exposure compensation and thus hinder a disease-originated difference in exposure level from being compensated in order not to adversely affect the medical diagnoses in, for example, radiograph for medical use.

It is also possible to determine whether or not image pickup is to be performed with the radiation dose adjusted, based on the information of the transmitted dose of radiation. This permits selective pickup of an image which involves no radiation adjustment.

In this case, a radiation projected image may be picked up by irradiating the radiation transmitted through a irradiation target on an accumulation type radiation/image converting panel to accumulate the information of a radiation image thereon, and reading the accumulated information with exciting light.

Further, it is preferable that the radiation beam for scanning the irradiation target take a form of a fan beam.

The radiation dose may be controlled by using shutter members to adjust the opening area of a collimator which forms the radiation beam.

It is preferable, particularly in the arrangement employing the mentioned accumulation type radiation/image converting panel, that the information of the transmitted dose of radiation necessary to determine the control dose of radiation be acquired by a detector, which is provided between the irradiation target and image pickup means and is designed to pass radiation therethrough.

The arrangement may be modified in much a way that the irradiation target is scanned with multiple radiation beams in the forward and backward scanning directions, so that while the irradiation target is scanned with the radiation beam in the forward scanning direction having a given radiation dose to detect the information of the transmitted dose of radiation in the image pickup involving this radiation beam, the adjustment of radiation corresponding to the information of the dose of transmitted radiation is performed in the image pickup involving the radiation beam in the backward scanning direction. In other words, a multiple image pickup (multi-exposure) is executed with multiple radiation beams.

With this arrangement, the result of the image pickup by the radiation beam in the forward scanning direction can immediately be reflected on the image pickup by the radiation beam in the backward scanning direction, thus ensuring a faster multiple image pickup to acquire the proper exposure.

In determining the control dose of radiation based on the information of the transmitted dose of radiation acquired using a radiation beam having a given dose of radiation, it is preferable that the control dose of radiation be determined on the basis of profile information and histogram information, which are acquired from the information of the transmitted dose of radiation.

Other objects and features of the present invention will be apparent from the following description of preferred embodiments in conjunction with the accompanying drawings.

BRIEF DESCRIPTION OF THE DRAWINGS

FIG. 4A and 4B are diagrams exemplifying histograms of the transmitted dose of radiation acquired by the first scanning (the first image pickup) according to the first embodiment;

FIG. 4C is a diagram exemplifying a profile made by the transmitted dose of radiation acquired by the first scanning (the first image pickup) according to the first embodiment;

FIG. 5 is a schematic system diagram illustrating a radiation image pickup method and apparatus according to a second embodiment of the present invention;

DETAILED DESCRIPTION OF THE PREFERRED EMBODIMENTS

Preferred embodiments of a radiation image pickup method and apparatus according to the present invention will now be described referring to FIGS. 1 to 9.

Figure 1:
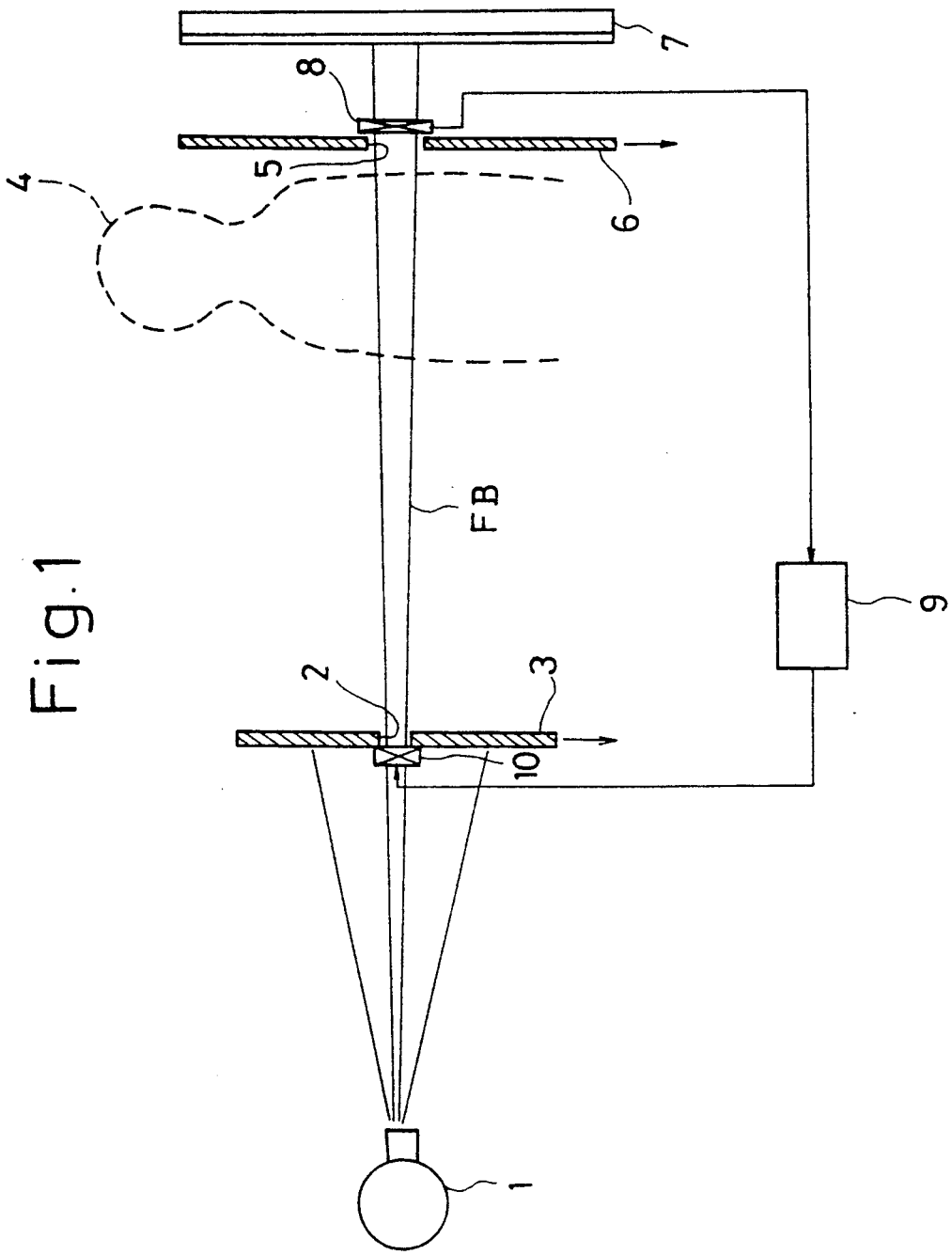
FIG. 1 is a schematic system diagram illustrating a radiation image pickup method and apparatus according to a first embodiment of the present invention.

FIG. 1 illustrates the structure of a radiation image pickup apparatus according to one embodiment. A first collimator 3 with a horizontally long slit 2 is positioned in front of an X-ray tube 1 as radiation source. The first collimator 3 is so designed as to be movable upward and downward by an actuator (not shown) which is controlled by a scan control unit 9. In association with this parallel movement, a fan beam FB (radiation beam) to be formed by the slit 2 is to scan in a direction perpendicular to the lengthwise direction of the slit. A stepping motor or an electromagnet may be used as the actuator.

A human body 4 (an object) as an irradiation target is placed at the scanning position of the fan beam FB formed by the slit 2 of the first collimator 3. Behind the human body 4 is a second collimator 6 with a horizontally oblong opening 5, which passes therethrough the fan beam FB that has passed through the human body 4.

The second collimator 6 is designed to be shiftable up and down in accordance with the up-and-down movement of the first collimator 3, by an actuator (not shown) which is controlled by the control unit 9. The fan beam FB having passed through the human body 4 travels through the opening 5 of the second collimator 6, reaching a film cassette 7 serving as an image pickup means.

The film cassette 7 comprises a front screen, an X-ray film and a background screen, to pick up and record the radiation image of the human body 4 with the irradiated radiation beam.

Between the opening 5 of the second collimator 6, i.e., the human body 4 as the irradiation target, and the film cassette 7 as the image pickup means, a line detector 8 of X-ray transmissive type is provided as a means to detect the dose of radiation transmitted through the human body 4.

The line detector 8 has separate X-ray sensor elements for each area, which is divided into multiple regions in the lengthwise direction of the opening 5 or the lengthwise direction of the fan beam FB. The individual sensor element detects the dose of irradiated radiation (dose of radiation transmitted through the human body 4), and sends a detection signal according to the detected radiation dose to the control unit 9. It is therefore possible to make the profile of the dose of radiation transmitted in the lengthwise direction of the opening 5.

The line detector 8 may be placed behind the film cassette 7 to detect the dose of radiation transmitted through the cassette 7, thereby the reduction of the radiation dose for image pickup may be deterred.

The number of the sensor elements of the line detector 8 is preferably 30 to 600 and particularly desirably 50 to 200 for practical use. Further, 50 to 200 pieces of data, rather than 30 to 600, are suitable as the quantity of data in the scanning direction of the detector 8 (in the vertical direction). The quantity of data may be reduced down to the required amount by an averaging process or the like.

A modulator 10 is provided as a radiation-dose controlling means in the slit 2 of the first collimator 3. The modulator 10 variably controls the opening area of the slit 2 for individual areas divided into multiple regions along the slit 2 to thereby variably adjust the dose of radiation transmitted through the slit 2 (exposure to the human body 4) at multiple points along the slit 2.

Figure 2:
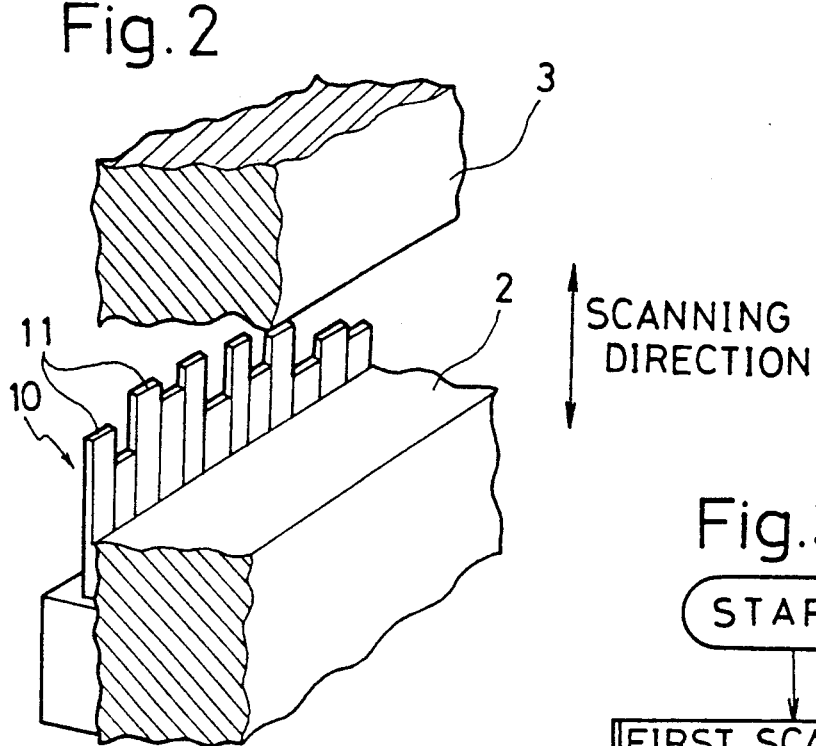
FIG. 2 is a partially enlarged perspective view illustrating a modulator shown in FIG. 1.

As shown in FIG. 2, the modulator 10 is provided with multiple shutter members 11 made of a radiation-absorbing material. Each shutter member 11 is supported movable in the width direction of the slit 2 almost along the end face of the first collimator 1 on the side of the X-ray tube 1. The shutter members 11 are arranged without seam adjacent to one another along the slit 2. Each shutter member 11 has an actuator provided at its proximal end, so that the shutter members 11 can independently move forward and backward in the mentioned moving direction by the associated actuators.

It is therefore possible to selectively shift the shutter members 11 in the direction to cover the opening of the slit 2 to alter the opening area of the slit 2 in the lengthwise direction thereof, thereby permitting control of the transmitted dose of radiation in the lengthwise direction of the slit 2. If the number of the shutter members 11 is approximately equal to the number of the sensor elements of the detector 8, provided side by side in the lengthwise direction of the opening 5 of the detector 8, the transmitted dose of radiation to the human body 4 can be controlled in accordance with the radiation dose detected by each sensor element.

While the shutter members 11 constituting the modulator 10 are designed to be linearly movable in the width direction of the slit 2, the members 11 may be designed swingable rotatable as long as the opening area of the slit 2 can be changed in its lengthwise direction.

A description will now be given of the sequence of image pickup processes which is controlled by the control unit 9 in the thus constituted radiation image pickup apparatus (particularly, in an X-ray examination apparatus for medical uses), referring to the flowchart in FIG. 3.

Figure 3:
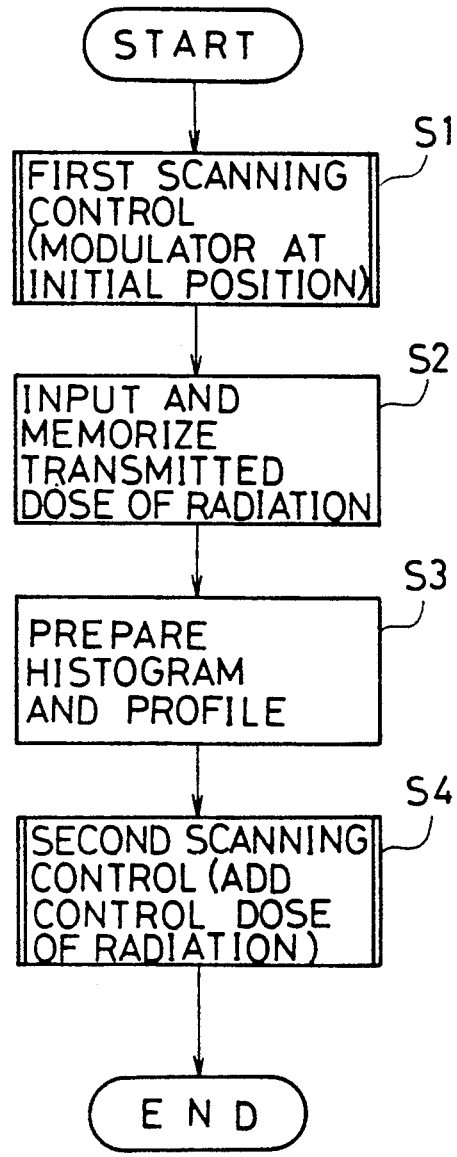
FIG. 3 is a flowchart illustrating how to control image pickup according to the first embodiment.

The function of the first scanning control means, radiation control dose setting means, second scanning control means and multi-image forming control means in this embodiment are provided in the form of software as shown in FIG. 3.

With the individual shutter members 11 of the modulator 10 returned to the initial positions (i.e., with the control of the radiation dose by the modulator 10 canceled and the radiation dose of the fan beam FB set constant), scanning with the fan beam FB starts at a predetermined initial point (S1).

At this time the fan beam FB having passed through the human body 4 is irradiated via the opening 5 of the second collimator 6 on the detector 8, which in turn acquires the information of the transmitted dose of radiation, and the fan beam FB after passing through the detector 8 reaches the film cassette 7, forming a radiation projected image (first image pickup).

As the detector 8 detects the dose of radiation transmitted through the human body 4 in the first scanning, the detector 8 sequentially outputs a signal representing the detection result to the control unit 9, which in turn stores the signal (S2).

Based on the information of the dose of radiation transmitted through individual portions of the human body 4 stored in the first scanning, the control unit 9 prepares histograms of the dose of radiation passed through the human body 4 as shown in FIGS. 4A and 4B and a profile of the transmitted dose of radiation for each scanning position as shown in FIG. 4C (S3).

Based on the histograms and/or the profile, acquired in the first scanning, the underexposed portion in the first scanning is determined. The control dose of the radiation in the second scanning (second image pickup) is two-dimensionally determined in order to re-expose the underexposed portion. The second scanning (second image pickup; multi-exposure) is carried out while controlling the opening area of the fan beam FB by means of the modulator 10 in accordance with the determined control dose (S4).

The following will discuss how to determine the control dose of radiation in the second scanning based on the information of the transmitted dose of radiation acquired in the first scanning.

FIG. 4C illustrates the profile of a human body 4 having properly-functioning lungs in comparison with the profile of a human body 4 with one lung removed, the latter based on the actual detection results. For the human body 4 with one lung removed, the profile clearly differs from the normal profile; the dose of radiation transmitted through where one lung has been removed is smaller than the one acquired for the normal case. This difference will be detected, so that the portion which is expected to have the lung-removed portion is considered as the portion for which radiation adjustment should be stopped, and the second scanning (multi-image pickup) is executed while partially stopping the radiation adjustment by the shutter members 11 to prohibit exposure compensation.

This feature can prevent the underexposure of the lung removed portion from being undesirably compensated for, which otherwise provides a radiation image that cannot clearly indicate the lung removal.

The above decision may also be made based on the histograms of the transmitted dose of radiation as presented in FIGS. 4A and 4B.

Alternately, these histograms may be used in combination with the profile given in FIG. 4C.

The arrangement may be modified in much a way that if there is any underexposed portion, such as the lung-removed portion, which should not be subjected to exposure compensation in the second scanning, the second scanning will not be performed at all, and a radiation projected image will be obtained only by the first scanning.

Using the profile shown in FIG. 4C, it can be determined that the mediastinum portion including the heart is underexposed as compared with the lung portion. The second scanning (second image pickup) to provide multi-image forming (exposure) can be performed to compensate for such underexposure.

In the second scanning, the shutter members 11 of the modulator 10 control the opening area of the slit 2 in such a way that the radiation dose to any portion underexposed in the first scanning, including the mediastinum portion containing the heart, becomes greater than the radiation dose to the portion properly exposed in the first scanning. The adjustment of the slit's opening area permits the underexposed portion to be exposed again to thereby increase the exposure level of such underexposed portion.

As described above, whether or not the second scanning (the second image pickup) should be performed is determined referring to a histogram and/or a profile based on data about the radiation dose collected in the first scanning (the first image pickup). In the case where the second scanning does not need to be performed, the image pickup will be terminated after completion of the first scanning, and a projection image exposed only in the first scanning will be recorded in the film cassette 7.

When it is determined that the second scanning is necessary, to optimize the exposure level, the second scanning is performed to reexpose the underexposed portion while protruding and retracting the shutter members 11 of the modulator 10 in accordance with the profile prepared in the first scanning to control the irradiation dose to the human body 4. The resultant image is then superimposed on the image acquired in the first scanning.

Further, in the second scanning, based on the data about the transmitted dose of radiation acquired in the first scanning as described above, controlling the radiation dose with respect to a specific portion, though underexposed, may be inhibited. Such control is realized by a partial dose control means.

According to this embodiment, as described above, normal image pickup is performed in the first scanning while the radiation dose in the lengthwise direction of the fan beam FB remains in a steady level, and in the second scanning, and image is exposed and superimposed on the image picked up in the first scanning while the radiation dose in the lengthwise of the fan beam FB is variously controlled. Therefore, as compared with image pickup done only by single scanning, the desired exposure level can be secured even with the output of the X-ray tube 1 kept low, which can reduce the load of the X-ray tube 1.

The second scanning can be omitted, based on the data about the transmitted dose of radiation collected in the first scanning. It is therefore possible to avoid providing a photograph which shows incorrect conditions or states of the human body 4, due to unnecessary multi-exposure, and to decrease the exposure dose to the human body 4.

Further, since the underexposed portion can be compensated for by the second scanning, more information can be involved in a radiograph. Some unnecessary portions can remain underexposed in the radiograph, which contributes to optimization of diagnoses of diseases referring to the radiograph, for example.

An X-ray sensitive film is used as an image pickup means in this embodiment, and in addition to the film, a fluorescent display screen or and electronic image amplifying tube may also be used. The image pickup means may comprise the same elements as transmitted-radiation dose detecting means.

In addition, as disclosed in Japanese Unexamined Patent Publication Nos. Sho 55-12144 and 63-189853, the image pickup means may be designed so that radiation transmitted through the human body 4 is irradiated on an accumulation type radiation/image converting panel (stimulable phosphor) and is accumulatively recorded on radiation image information, and the radiation image information recorded in the panel is read out with exciting light, such as a laser beam, and is processed as an electric image signal.

In the system using such stimulable phosphor, the accumulation type radiation/image converting panel comprising the stimulable phosphor replaces the film/-screen employed in the above-described embodiment.

According to another system employing a stimulable phosphor, scanning with a fan beam FB with a relatively low, constant radiation dose is executed while the control of the radiation dose by the modulator 10 is canceled, radiation transmitted through the irradiation target is irradiated on the stimulable phosphor to be accumulatively recorded on the radiation image information acquired in the first scanning, the accumulated radiation energy is converted into light using the exciting light, the converted light is detected by a photoelectric converting element, and then the radiation image in the first scanning which does not need radiation dose control by the modulator 10 is recorded as an electric image signal.

Based on the information acquired in the first scanning, the control dose of the radiation in the second scanning is two-dimensionally determined. The second scanning is carried out while protruding or retracting the shutter members 11 of the modulator 10 based on the determined dose, thereby providing a radiation image in the second scanning as per the above-described embodiment. This image is subjected to signal processing to be superimposed on the image acquired in the first scanning, thus permitting the same combined image as acquired by multi-exposure on a film to be recorded in the form of an electric image signal.

In the above system, the image pickup means using a stimulable phosphor also serves as the transmitted-radiation dose detecting means.

The modulator 10 may be designed to control the exposure by means of a filter device capable of altering its radiation (such as X-ray) absorbing property in addition to the design of this embodiment which variably adjusts the opening area of the slit 2. Further, the modulator 10 may be designed to have a combined function of the radiation absorbing member and the opening-area controlling member.

The shutter members 11 each may be shaped into a wedge whose thickness varies in the moving direction, so that both of the slit's opening area and the radiation transmittance of the shutter members 11 can be changed to control the transmitted dose of radiation. The number of the shutter members 11 is preferably 30 to 300, and the particularly preferable number would be 50 to 200. As the number of the shutter members 11 increases, even an image signal necessary for medical diagnoses will disappear by the multi-image forming. The number of the shutter members 11 should therefore be determined in the light of this phenomenon.

While the foregoing description of this embodiment has been given with reference to a chest X-ray examination apparatus for medical uses, this embodiment may also be applied to a radiograph apparatus, which is used for industrial purposes, such as inspection of internal defects of machine parts. In this case the radiation is not limited to X-rays, but may take other forms as well such as γrays.

The output of the X-ray tube 1 may be further reduced to leave a possibility that an underexposed portion will be present even after the first scanning and second scanning are performed, and a third or further scanning may be performed to compensate for this underexposure. This would however result in a longer photographing time.

In executing the multi-image forming, the slit width in the second scanning may be set different from the slit width in the first scanning.

The arrangement of a radiation image pickup apparatus according to the second embodiment of the present invention is shown in FIG. 5. Those elements corresponding to or identical to those of the first embodiment shown in FIG. 1 are given the same reference numerals to avoid repeating the same description.

In the apparatus shown in FIG. 5, a fan beam scans downward from the top in the diagram. A first collimator 3 has horizontally long slits 2a and 2b formed at a given interval. The slits 2a and 2b each form a fan beam FB. A second collimator 6 has two openings 5a and 5b in association with the fan beams FB formed by the two slits 2a and 2b.

A modulator 10, the same type as shown in FIG. 1, is provided at the slit 2a, located rearward in the scanning direction. A detector 8, the same type as shown in FIG. 1, is provided at the opening 5b, located in the frontward in the scanning direction.

With the above arrangement, the fan beam FB(1) formed by the slit 2b is irradiated onto a human body 4 without having its radiation dose in the lengthwise direction variably controlled, and the radiation transmitted through the body 4 is detected by the detector 8. The detected radiation is exposed on a film cassette 7.

The fan beam FB(2) formed by the slit 2a, which scans as if to follow the former fan beam FB(1), will have its radiation dose variably at multiple points in the lengthwise direction by the modulator 10. This dose-controlled fan beam FB is then irradiated on the human body 4, and the radiation transmitted through the body 4 is exposed directly on the film cassette 7 without going through the detector 8.

According to the second embodiment shown in FIG. 5, therefore, the two fan beams FB are permitted to scan once at the same time to realize double exposure on the film cassette 7. First, while uniform radiation is irradiated using the fan beam FB(1) frontward in the scanning direction to form an image, the dose of radiation transmitted through the human body 4 is detected by the detector 8. The fan beam FB(2) rearward in the scanning direction is reexposed on the film cassette 7 while adjusting the opening area of the slit 2a by the modulator 10, in order to compensate for exposure of an underexposed portion where the radiation dose of the fan beam FB(1) is detected low by the detector 8.

With this arrangement, to compensate for exposure of the underexposed portion in the second scanning using the fan beam FB(2), the necessary exposure for that portion of the body 4 which does not easily pass radiation therethrough has only to be acquired in two exposing processes involving the fan beams FB(1) and (2) as per the first embodiment. The output of the X-ray tube 1 can be set lower than what is required in the case of forming an image only by a single exposure.

Data about the transmitted dose of radiation is collected prior to the second scanning with the fan beam FB(2). When it is considered unnecessary, based on this data, to perform the second scanning for exposure compensation on, for example, a scan area lying ahead from a certain portion, control to avoid the unnecessary exposure can easily be effected by causing the modulator 10 to close the slit 2a.

Further, if information of a specific portion for which reexposure is undesirable is available in advance, it is possible to compensate for exposure of only the underexposed portion excluding this specific portion.

Furthermore, the image pickup time required in this embodiment can be made shorter than the time needed in the case where a single radiation beam is used twice to execute two scannings for multi-image pickup.

While, in the second embodiment, the double exposure is effected by the fan beams (1) and (2), three or more slits may be provided to form three or more fan beams which are used to scan a human body at the same time, so that the transmitted dose of radiation is detected also by the second scanning fan beam to further compensate for exposure of an underexposed portion using the next fan beam. In this case, the output of the X-ray tube 1 can be reduced further, which is very desirable.

Figure 6:
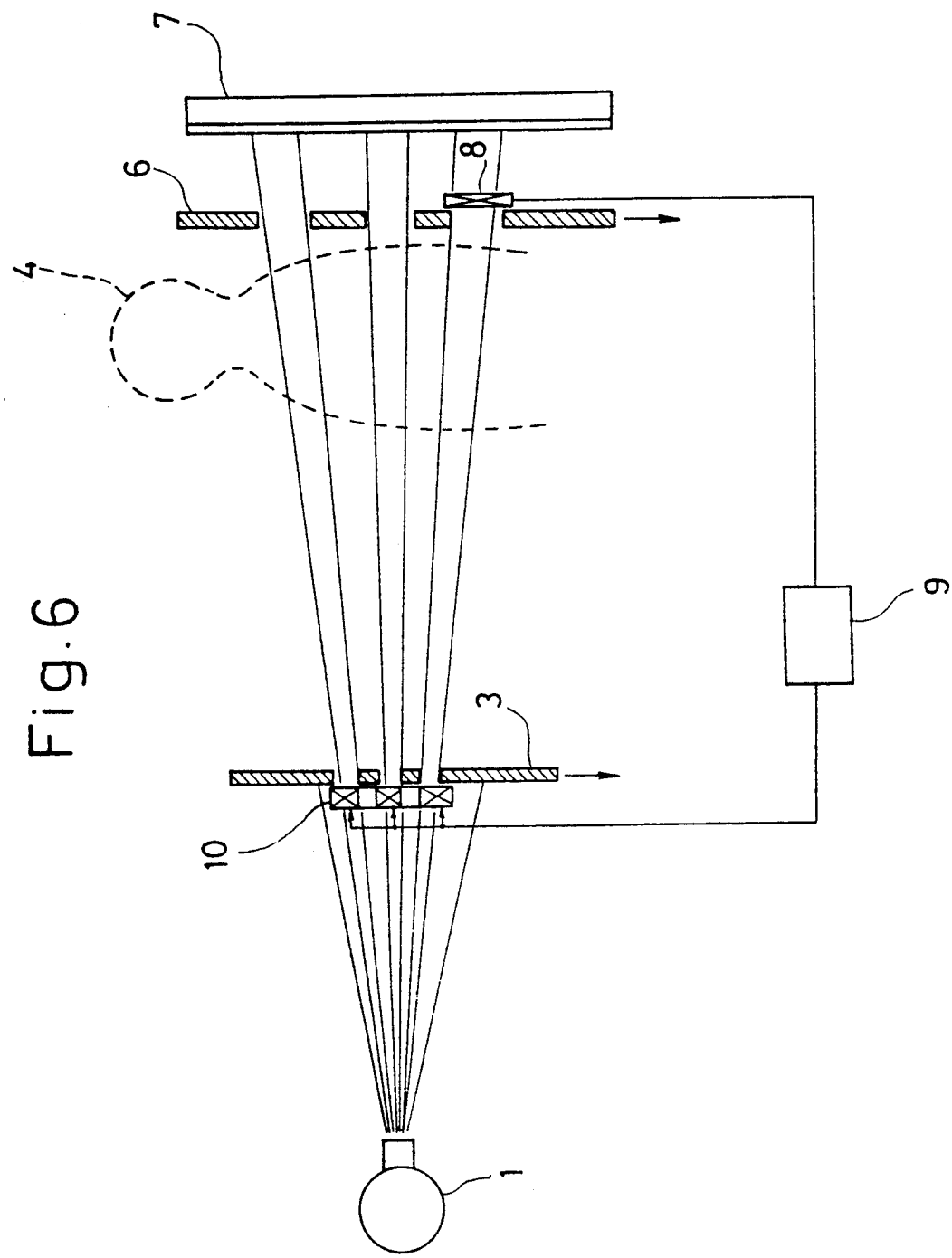
FIG. 6 is a schematic system diagram illustrating a radiation image pickup method and apparatus according to a third embodiment of the present invention.

In the case where three or more slits are provided as described above, independently operable modulators 10 may be provided for the respective slits as shown in FIG. 6, thereby permitting the number of X-rays in the first scanning to be controlled by altering the slit width, or allowing for arbitrary selection of a slit which passes the X-rays therethrough in the second scanning to compensate for exposure.

According to the above-described embodiments, a fan beam is formed as a radiation beam. Provided that the same arrangement is used, it is apparent that a pencil spot for scanning an irradiation target in the form of a spot produces the same effect as the fan beam. Since the pencil beam involves complicated scanning movement and takes longer scanning time (image-pickup time); however, scanning with the fan beam is more preferable.

The fan beam may scan in the horizontal direction perpendicular to the scanning direction employed in the first to third embodiments.

Each of the foregoing embodiments prevents degradation of diagnostic performance due to unnecessary control of the dose of radiation by carrying out the first image pickup operation, in which the dose of radiation is constant, and the second image pickup operation which controls the dose of radiation on the basis of the information of the transmitted dose of radiation obtained by the first image pickup.

However, the following fourth embodiment of the present invention obtains an image of the case where the dose of radiation is not controlled or an image of the case where the degree of control is lowered, by image signal processing on the basis of the result of one image pickup operation carried out while the dose of radiation is fed back and controlled. Therefore, those portions which become ambiguous in the image obtained by controlling the dose of radiation can be confirmed clearly on the basis of the image which is obtained by image signal processing described above, and degradation of diagnostic performance resulting from the unnecessary control of the dose of radiation can be avoided in the same way as in the foregoing embodiments. Another advantage that cannot be obtained by the foregoing embodiments is that image pickup is possible only once.

Figure 7:
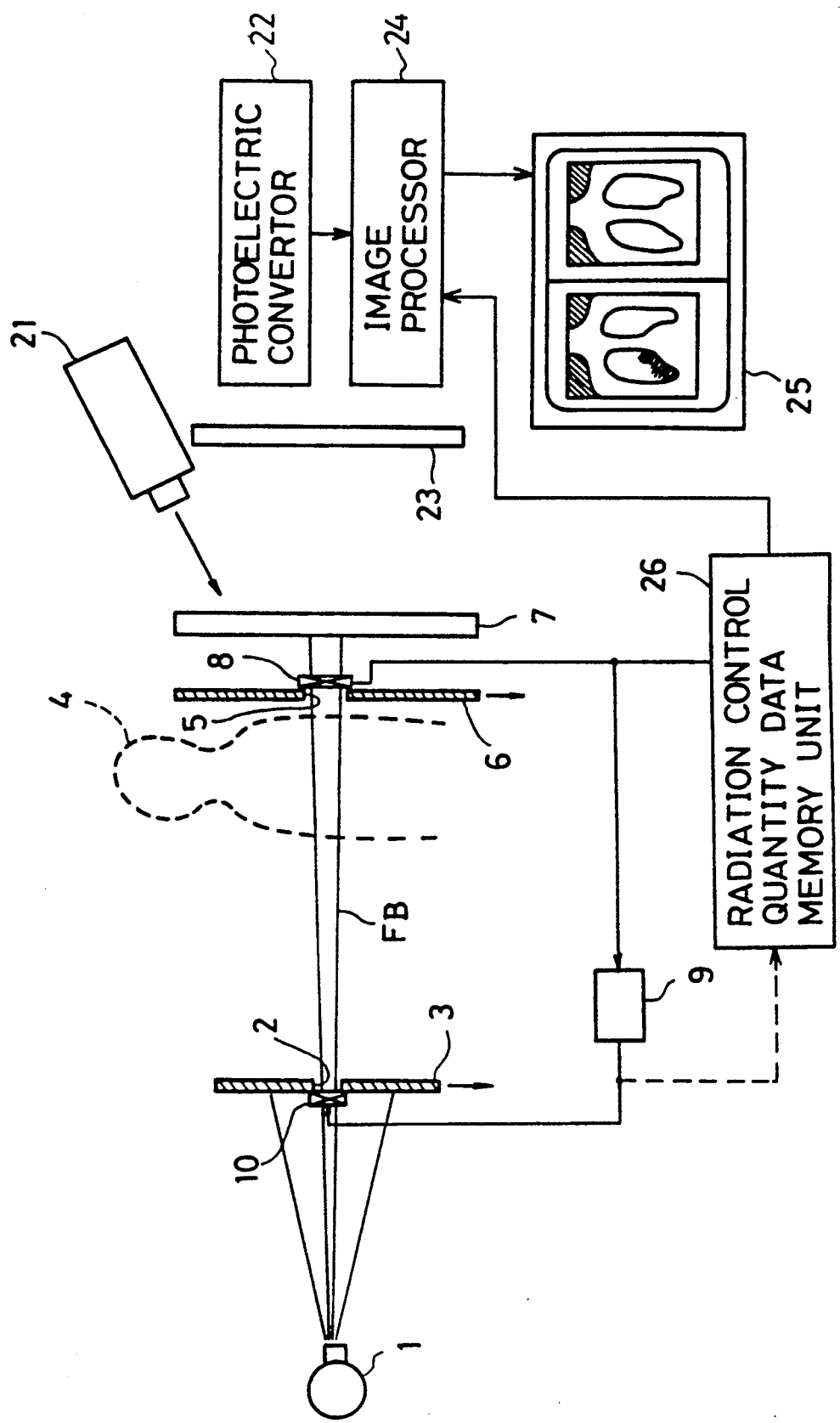
FIG. 7 is a schematic system diagram illustrating a radiation image pickup method and apparatus according to a fourth embodiment of the present invention.

In FIG. 7 showing the construction of the radiation image pickup apparatus according to the fourth embodiment, like reference numerals are used to identify like constituents as in FIG. 1, and the detailed explanation of the common constituents is omitted. In FIG. 7, however, reference numeral 7 does not denote the film cassette but does a stimulable phosphor panel.

The stimulable phosphor panel 7 is obtained by disposing a stimulable phosphor layer on a support by vapor deposition of the stimulable phosphor or by coating a stimulable phosphor paint. The stimulable phosphor layer is shielded or covered with a protective member so as to prevent any adverse influences of environmental conditions. The materials described in Japanese Unexamined Patent Publication No. 61-72091 or in Japanese Unexamined Patent Publication No. 59-75200 are used for the stimulable phosphor material.

The control unit 9 controls the modulator 10 on the basis of the data of the transmitted dose of radiation (low spatial frequency components) of the human body 4 detected by the detector 8, and records the radiation image on the stimulable phosphor panel 7 while controlling the transmitted dose of radiation radiated to the human body 4.

With this construction, the transmitted dose of radiation of the human body 4 is fed back to the stimulable phosphor panel 7 by the construction comprising the detector 8, the control unit 9 and the modulator 10, and the radiation image picked up is recorded on the stimulable phosphor panel 7. Such a control operation of the dose of radiation simultaneously picks up the image of the portions, which are easily transmissible to the radiation, such as the lung, and the portions, which are transmissible with difficultly, such as the bones and the abdomen, under an easily observable state.

On the other hand, readout of the image information from the stimulable phosphor panel 7 on which the radiation image information of the object is accumulated and recorded is carried out in the following way.

A stimulable excitation light source (gas laser, solid laser, semiconductor laser, etc.) 21 generates an excitation optical beam having a controlled outgoing intensity, and the excitation optical beam scans the stimulable phosphor panel 7 on which the radiation image information of the object is built up and recorded, and radiates radiation energy (latent image) stored in the stimulable phosphor panel 7 as phosphorescence (stimulable phosphorescence).

A photoelectric convertor 22 receives the phosphorescence (stimulable phosphorescence) obtained by scanning of the stimulable phosphor panel 7 by the excitation optical beam through a filter 23 which passes only this phosphorescence, converts it photoelectrically to a current signal corresponding to the incident beam, and obtains a radiation image signal.

The analog radiation image signal read photoelectrically by the photoelectric convertor 22 is sequentially converted from an analog signal to a digital signal (A/D) by an A/D convertor, and is outputted to an image processor 24 as a digital radiation image signal. This image processor 24 applies various image processings (tone wedge processing, frequency processing, etc.) to the digital radiation image signal, converts it to a form suitable for diagnosis and then outputs the signal to a radiation image reproduction apparatus 25.

The radiation image reproduction apparatus 25 is a monitor such as a printer, a CRT, etc., inputs the digital radiation image signal processed by the image processor 24, and visualizes the radiation image picked up as a hard copy or a reproduction screen.

The radiation image signals outputted from the image processor 24 may be preserved by disposing a recording system (filing system) such as a semiconductor memory device with, or in place thereof, the radiation image reproduction apparatus 25.

Besides the known processings such as tone wedge processing and frequency processing, the image processor 24 executes signal processing based on the control quantity of the radiation. In this fourth embodiment, the radiation image when the dose of radiation is not controlled can also be obtained by executing signal processing of the radiation image on the basis of the control quantity data, in addition to the radiation image obtained by controlling the dose of radiation by the modulator 10.

To execute such a signal processing on the basis of the control quantity data of the radiation, there is disposed a radiation control quantity data memory unit 26 which stores the detection signals by the detector 8 or the control signals of the modulator 10 on the basis of the detection signals, as the control quantity data of the radiation. The digital radiation image signal input from the photoelectric convertor 22 is processed by the image processor 24 on the basis of the control quantity data of the radiation at the time of pick-up, which is stored in this radiation control quantity data memory unit 26, to obtain approximately a radiation image which is expected to be obtained when the radiation is not controlled.

Figure 8:
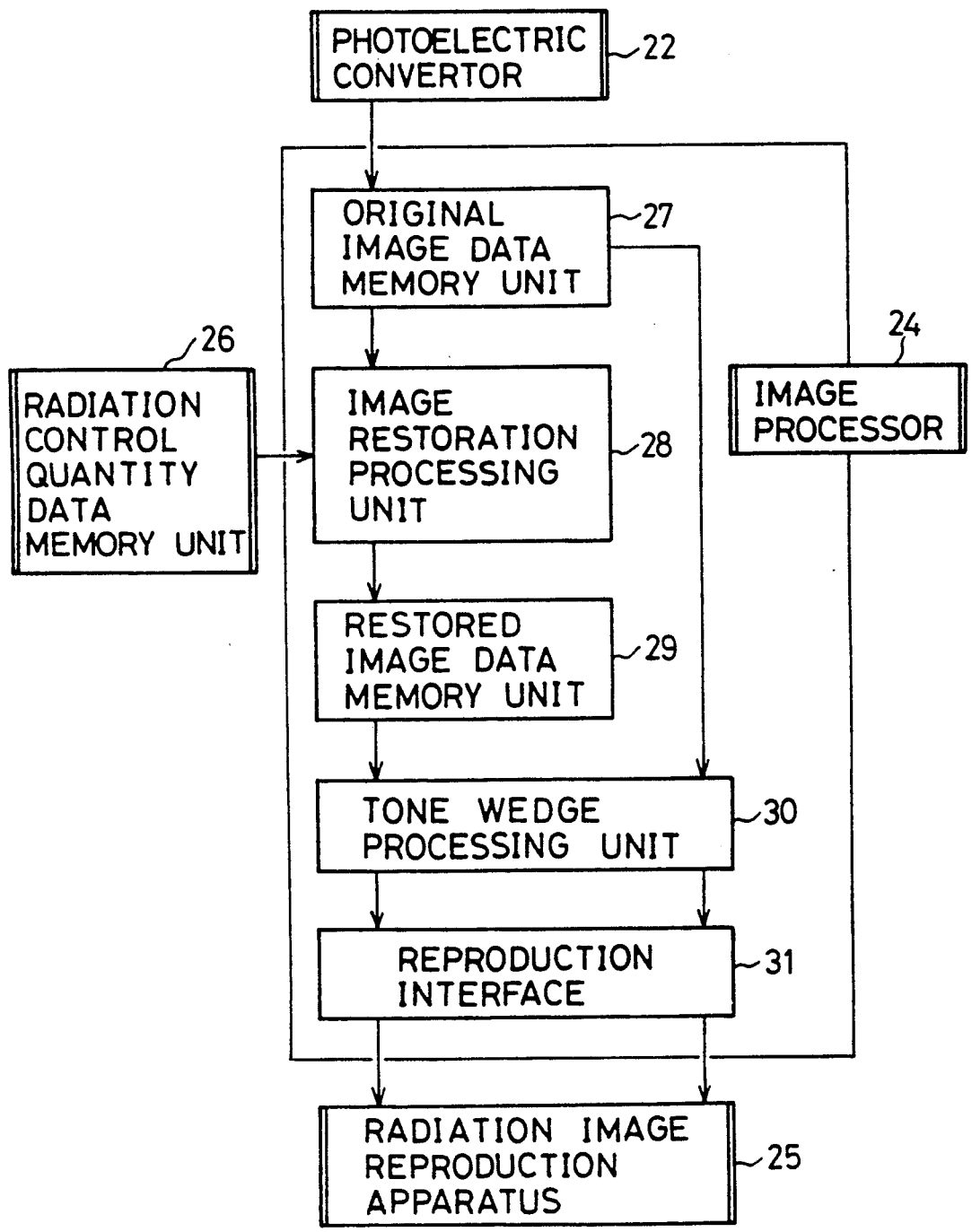
FIG. 8 is a block diagram illustrating a detailed structure of an image processor in FIG. 7.

FIG. 8 is a structural block diagram of the image processor 24 described above. The radiation image signal obtained by controlling the dose of radiation input from the photoelectric convertor 22 is once stored in an original image data memory unit 27.

An image restoration processing unit 28 approximately obtains an image, when the dose of radiation is not controlled, by processing the radiation image signal picked up by controlling the dose of radiation and stored in the original image data memory unit 27, on the basis of the control quantity data stored in the radiation control quantity data memory unit 26.

The radiation image signal obtained as a result of processing by the image restoration processing unit 28 is stored in a restored image data memory unit 29.

Figure 9:
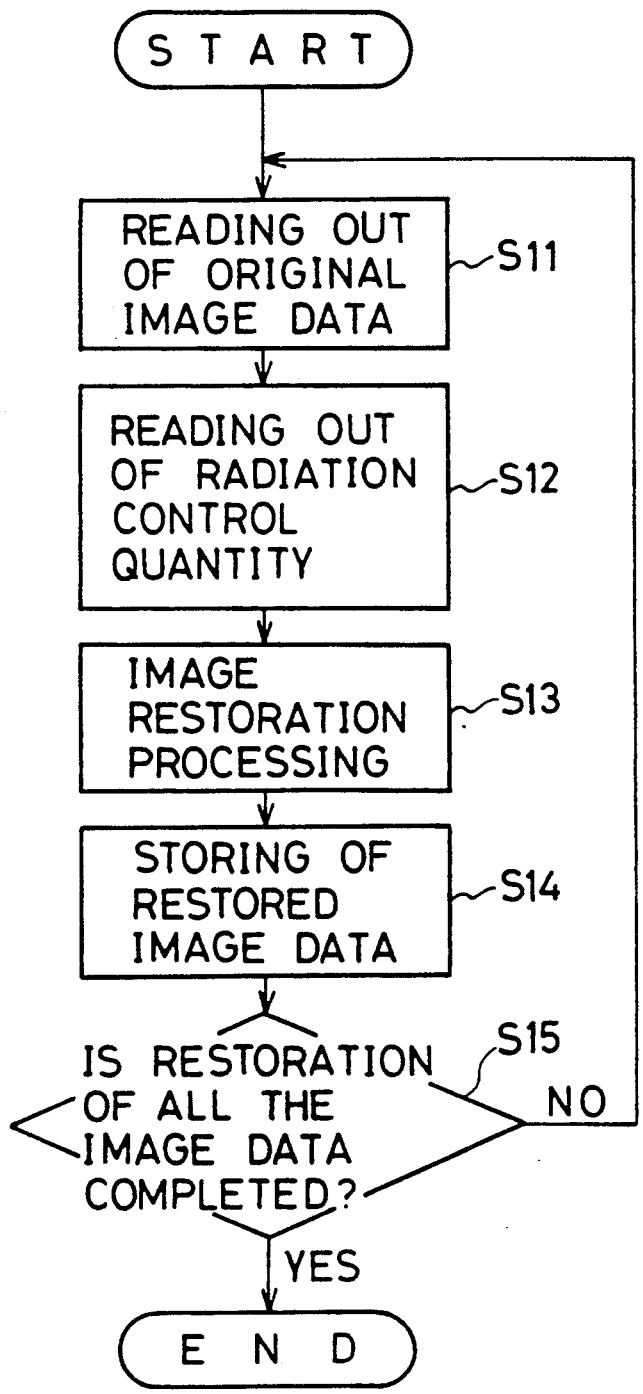
FIG. 9 is a flowchart showing the mode of an image restoration control according to the fourth embodiment.

FIG. 9 is a flowchart and shows the mode of signal processing carried out in the image restoration processing unit 28.

In the flowchart of FIG. 9, the image data for each pixel stored in the original image data memory unit 27 is read out at step 11 (S1 in the flowchart), and the data of the radiation control quantity corresponding to the same image area as the image data read out at step 11 is read out from the radiation control quantity memory unit 26 at the next step 12.

The original image data is processed at step 13 on the basis of the radiation control quantity data. More definitely, if the image data are those image data which are obtained in the image area for which control of reducing the dose of radiation to 50% is effected, for example, and the image data, when the dose of radiation is not reduced to 50% in signal processing, can be obtained by doubling the image data, because the radiation in the dose twice that of the image pick-up when the radiation dose is not controlled is radiated when the dose of radiation is not controlled, provided that the image data correspond linearly to the transmitted dose of radiation. In other words, the radiation image (reconstructed image), which is obtained when the dose of radiation is not controlled in signal processing, can be obtained approximately by adding compensatingly the signals so as to compensate for the dose of radiation which is not reduced and controlled by the modulator 10.

The image data restored at step 13 is sequentially stored in the restoration image data memory unit 29 at step 14.

Whether or not restoration processing in the pixel unit is completed for all the image data is judged at step 15, and if not, the flow returns again to step 11 and the procedures of step 11 to step 14 are repeated.

As described above, the image signal obtained by controlling the dose of radiation stored in the original image data memory unit 27 and the image signal when the dose of radiation obtained by the image signal described above, and stored in the restoration image data memory unit 29 is not controlled, are subjected to image processing such as tone wedge processing by a tone wedge processing unit 30, respectively, and are output and visualized to and by the radiation image reproduction apparatus 25 through a reproduction interface 31.

Accordingly, the original image obtained by controlling the dose of radiation and the image corresponding to the case where this image is signal processed and the dose of radiation is not controlled are respectively outputted to the radiation image reproduction apparatus 25, and the radiation image reproduction apparatus 25 aligns and reproduces the two images obtained by imaging the same human body 4 on the CRT or the film as shown in FIG. 7.

As described above, the fourth embodiment deliberately obtains the image of the case where the dose of radiation is not controlled, on the basis of the image obtained, in contrast with the image pickup operation which controls the dose of radiation in order to obtain a radiation image permitting easy observation of the portions which are easily transmissible to the radiation and the portions which are transmissible with difficultly. The necessity for such a processing and the effects brought forth by the processing will now be explained.

When the image is picked up by controlling the dose of radiation by the modulator 10, the exposure level can be converted to a suitable range without being affected by the differences of the thickness and absorptivity at the image pickup portion of the object as described above, but such control of radiation sometimes results in the problem that the lesion portion which distinctively appears when control is not made becomes ambiguous.

For instance, when a lesion occurs in the lung within a limited range, it is not controlled by the modulator 10, but when the lesion expands over a wide range, the transmitted dose of radiation drops at this lesion portion. When the modulator 10 controls the dose of radiation in a contracting direction, therefore, control of reducing the dose of radiation to the normal portions of the lung is relatively carried out in such a manner as to increase the transmitted dose of radiation at such lesion portion as compared with the other portions, so that the distinction between the normal lung and the lesion lung becomes ambiguous on the reproduced image.

When the modulator 10 is so controlled as to permit the passage of only a part of the ordinary X-rays and is opened, whenever necessary, so as to increase the X-ray quantity, the modulator 10 is opened so as to increase the dose of radiation at the lesion portion in such a manner as to compensate for the drop of the transmitted dose of radiation at the lesion portion if the lesion portion in which the transmitted dose of radiation drops exists over a wide range. In this case, too, the distinction between the normal lung the lesion portion becomes ambiguous on the reproduced image.

If the image obtained by controlling the dose of radiation and the image when the dose of radiation is not controlled are obtained simultaneously as in this fourth embodiment, however, the image obtained by controlling the dose of radiation makes it easy to simultaneously observe the portions where the radiation is easily transmissible and the portions where the radiation is not, and to visualize them, while the image when the dose of radiation is not controlled makes it possible to clearly diagnose the existence of the lesion portion.

The image pick-up operations need not be carried out individually in order to obtain these two images, but the two kinds of images can be obtained simultaneously by one image pick-up operation, so that the exposure of the human body 4 as the object can be restricted.

In the embodiment described above, the image signal when control is not at all carried out is obtained by the signal processing of the image when the dose of radiation is controlled, but it can be obtained by the signal processing of the signal when the degree of control is reduced, too. In this case, the image having the degree of control reduced to the half can be obtained by increasing 1.5 times the signal when the signal level at the time of non-control can be obtained by doubling the signal from the control quantity, for example. It is therefore possible to obtain a plurality of images, in which the degree of control is approximately changed with respect to the original image by changing the degree of control into a plurality of kinds in terms of signal processing.

When the image having the reduced degree of control is obtained by signal processing as described above, a level of reduction of the degree of control can be set to an arbitrary level by an external operation. Needless to say, an operation which visualizes only the original image having a controlled dose of radiation can be accomplished easily.

Furthermore, it is possible to obtain another image having a changed degree of control by preserving the image signal obtained by controlling the dose of radiation and the data stored in the radiation control quantity data memory unit 26 as a pair, and processing the image signal on the basis of the control quantity data at the time of reproduction, whenever necessary.

In the fourth embodiment described above, the image pick-up means 7 is the stimulable phosphor panel, but the radiation-sensitive film or a semiconductor detector may be used in the same way as in the first and second embodiments.

When the image is recorded on the film, the radiation image of the film is photoelectrically converted to the electric image signal, and then the processing on the basis of the radiation control quantity data is executed as described above.

When the semiconductor detector is used in place of the stimulable phosphor panel, the image data obtained from the semiconductor detector can be sequentially processed on the basis of the transmitted dose level (low spatial frequency components) detected at that time by the detector 8, and the radiation control quantity data memory unit 26 can be omitted in such a case.

I claim:

1. An apparatus for detecting an X-ray image comprising:
    a source of X-rays adapted to scan an irradiation target;
    a first collimator between said source and said target, said first collimator being movable in a scanning direction, and at least one opening wherein a first radiation beam is formed and is directed to said target in said scanning direction, and said opening having a diaphragm forming a second radiation beam;
    a detector for detecting said first radiation beam transmitted through said target, and outputting a strength signal based thereon;
    a controller for adjusting said diaphragm to form said second radiation beam based on said strength signal, and outputting an adjusting value of said diaphragm;
    an image pickup for receiving said second radiation beam after passage through said target;
    a first device for producing a first original image based on said first radiation beam and said second radiation beam transmitted through said target; and
    a second device for reproducing a second processed image based on said first original image formed by said image pickup and said adjusting value of said diaphragm, wherein said second processed image is formed based on said first radiation beam.

2. The apparatus of claim 1, wherein said image pickup further receives said first radiation beam, and said image pickup forms said first original image based on said first radiation beam and said second radiation beam.

3. The apparatus of claim 2 wherein said second beam is directed to a part of said target after said first beam has scanned said part but while said first beam is scanning said target.

4. The apparatus of claim 2 wherein said opening is a single opening.

5. The apparatus of claim 4, wherein said first collimator scans said target at least two times.

6. The apparatus of claim 5, wherein said diaphragm of said opening is divided into a plurality of sections, said sections are controlled independently by said controller so as to form said second radiation beam, and said sections of sad diaphragm is adjusted to a predetermined value in a first scanning and is adjusted based on said strength signal in a second scanning.

7. The apparatus of claim 6 further comprising a second collimator through which said first radiation beam and said second radiation beam pass which prevents dispersion of said first radiation beam and said second radiation beam, said second collimator moving in synchronism with said first collimator.

8. The apparatus of clam 6 wherein said first radiation beam and/or said second radiation beam after passage through said target are received on an accumulation type radiation image converting panel to be formed as an accumulated radiation image, said image pickup reading said accumulated radiation image by exciting light.

9. The apparatus of claim 6 wherein first opening is a slit and said first radiation beam and/or said second radiation beam is a fan beam.

10. The apparatus of claim 6 wherein said detector outputs a profile and/or histogram of said radiation image based on said strength signal stored in a first scanning and determines a control dose of radiation based on said strength signal.

11. The apparatus of claim 1, wherein said image pickup is a semiconductor detector.

12. The apparatus of claim 1, wherein said image pickup and said detector are semiconductor detectors.

13. The apparatus of claim 12, wherein said image pickup and said detector are common.

14. The apparatus of claim 1 wherein said opening is a single opening.

15. The apparatus of claim 14, wherein said first collimator scans said target at least two times.

16. The apparatus of claim 15, wherein said diaphragm of said opening is divided into a plurality of sections, said sections are controlled independently by said controller so as to form said second radiation beam, and said sections of said diaphragm is adjusted to predetermined value in a first scanning and is adjusted based on said strength signal in a second scanning.

17. The apparatus of claim 2 further comprising a second collimator through which said first radiation beam and said second radiation beam pass which prevents dispersion of said first radiation beam and said second radiation beam, said second collimator moving in synchronism with said first collimator.

18. The apparatus of claim 2 wherein said first radiation beam and/or sad second radiation beam after passage through said target are received on an accumulation type radiation image converting panel to be formed as an accumulated radiation image, said image pickup reading said accumulated radiation image by exciting light.

19. The apparatus of claim 1 wherein first opening is a slit and said first radiation beam and/or said second radiation beam is a fan beam.

20. The apparatus of claim 2 wherein said detector outputs a profile and/or histogram of said radiation image based on said strength signal stored in a first scanning and determines a control dose of radiation based on said strength signal.

* * * * *